United States Patent [19]
Radisch, Jr.

[11] Patent Number: 5,295,493
[45] Date of Patent: Mar. 22, 1994

[54] ANATOMICAL GUIDE WIRE

[75] Inventor: Herbert R. Radisch, Jr., San Diego, Calif.

[73] Assignee: Interventional Technologies, Inc., Calif.

[21] Appl. No.: 974,246

[22] Filed: Nov. 10, 1992

Related U.S. Application Data

[62] Division of Ser. No. 853,916, Mar. 19, 1992.

[51] Int. Cl.$^5$ .................................................. A61B 5/00
[52] U.S. Cl. ...................................... 128/772; 606/180
[58] Field of Search ................. 128/657, 772; 604/22, 604/95, 170, 285; 606/167, 170, 180

[56] References Cited

U.S. PATENT DOCUMENTS

| | | | |
|---|---|---|---|
| 1,060,665 | 5/1913 | Bell . | |
| 1,878,671 | 9/1932 | Cantor | 604/170 X |
| 1,920,006 | 7/1933 | Dozier | 604/170 |
| 2,574,840 | 11/1951 | Pieri et al. | 128/349 |
| 2,688,329 | 9/1954 | Wallace | 128/349 |
| 3,452,740 | 7/1969 | Muller | 128/2 |
| 3,467,101 | 9/1969 | Fogarty et al. | 128/348 |
| 3,528,406 | 9/1970 | Jeckel et al. | 129/2.05 |
| 3,547,103 | 12/1970 | Cook | 128/2.05 |
| 3,605,725 | 9/1971 | Bentov | 128/2.05 R |
| 3,612,058 | 10/1971 | Ackerman et al. | 128/348 |
| 3,618,614 | 11/1971 | Flynn | 128/348 |
| 3,731,671 | 5/1973 | Mageoh | 128/2.05 R |
| 3,789,841 | 2/1974 | Antoshkiw | 128/2.05 R |
| 3,811,449 | 5/1974 | Gravlee et al. | 128/343 |
| 3,906,938 | 9/1975 | Fleichhacker | 604/170 X |
| 3,913,568 | 10/1975 | Carpenter | 128/11 |
| 3,995,623 | 12/1976 | Blake et al. | 128/2.06 E |
| 4,003,369 | 1/1977 | Heilman et al. | 128/2 M |
| 4,033,331 | 7/1977 | Guss et al. | 128/2 M |
| 4,137,906 | 2/1979 | Akiyama et al. | 128/2 A |
| 4,195,637 | 4/1980 | Grüntzig et al. | 128/348 |
| 4,215,703 | 8/1980 | Willson | 128/772 |
| 4,245,624 | 1/1981 | Komiya | 128/4 |
| 4,257,421 | 3/1981 | Beal | 128/657 |
| 4,273,128 | 6/1981 | Lary | 128/305 |

(List continued on next page.)

OTHER PUBLICATIONS

Judkins, "Selective Coronary Arteriography" Radiology vol. 89 No. 5 pp. 815-824 Nov. 1967.

Hirvonen, James K., "Surface Modification of Polymers and Ceramics." *Advanced Materials & Process Magazine.* May, 1986.

"Nitrogen Implantation Into Steels." *Science and Engineering,* 90 (1987) 99-109.

Sioshansi, P., "Medical Applications of Ion Beam Processes." Apire Corporation, North-Holland Physics Publishing Division.

Hioki, T., Itoh, A., Noda, S., Doi, H., Sawamoto, J., Kimigaito, O., "Effect of Ion Implantation of Fracture Stress of $Al_2O_3$." *Nuclear Instruments and Methods in Physics Research.* North Holland, Amsterdam, (1988) 521-525.

Meier, B., Carlier, M., Finci, L., Nukata, E., Urban, P., Niederhauser, W., and Favre, J., "Magnum Wire for Balloon Recanalization of Chronic Total Coronary Occlusions," *The American Journal of Cardiology,* vol. 64, pp. 148-154, Jul. 15, 1989.

*Primary Examiner*—Max Hindenburg
*Attorney, Agent, or Firm*—Nydegger & Associates

[57] ABSTRACT

An apparatus for introducing an atherectomy cutter into a coronary artery for removing a stenosis from the artery, includes a guide wire having a predetermined anatomically shaped configuration. The guide wire may correspond in shape to an arterial path through the aorta and into an artery of the heart such as a right coronary artery (RCA), a left anterior descending artery (LAD), a left circumflex artery (LCX), or a bypass graft. A percutaneously inserted guiding catheter is used to direct the anatomically shaped guide wire into a selected coronary artery and to subsequently retrieve the guide wire from the artery. With the guide wire in place in the artery, and the guiding catheter removed from its engagement with the guide wire, the atherectomy cutter is slidingly engaged to the guide wire and is advanced along the wire into contact with the stenosis.

15 Claims, 3 Drawing Sheets

U.S. PATENT DOCUMENTS

| | | | |
|---|---|---|---|
| 4,307,722 | 12/1981 | Evans | 128/344 |
| 4,323,071 | 4/1982 | Simpson et al. | 128/343 |
| 4,362,163 | 12/1982 | Krick | 604/280 |
| 4,444,188 | 4/1984 | Bazell et al. | 128/348 |
| 4,456,017 | 6/1984 | Miles | 128/772 |
| 4,502,482 | 3/1985 | DeLuccia | 128/207.15 |
| 4,503,569 | 3/1985 | Dotter | 3/1.4 |
| 4,516,972 | 5/1985 | Samson | 504/282 |
| 4,545,390 | 10/1985 | Leary | 128/772 |
| 4,571,240 | 2/1986 | Samson et al. | 604/96 |
| 4,572,186 | 2/1986 | Gould et al. | 128/341 |
| 4,582,181 | 4/1986 | Samson | 128/348 |
| 4,586,923 | 5/1986 | Gould et al. | 604/95 |
| 4,589,412 | 5/1986 | Kensey | 128/305 |
| 4,616,653 | 10/1986 | Samson et al. | 128/344 |
| 4,650,466 | 3/1987 | Luther | 604/95 |
| 4,650,467 | 3/1987 | Bonello et al. | 604/95 |
| 4,655,214 | 4/1987 | Linder | 128/207.18 |
| 4,696,667 | 9/1987 | Masch | 604/22 |
| 4,728,319 | 3/1988 | Masch | 604/22 |
| 4,732,154 | 3/1988 | Shiber | 128/305 |
| 4,854,330 | 8/1989 | Evans, III et al. | 128/772 |
| 4,886,067 | 12/1989 | Palermo | 128/657 |
| 4,935,025 | 6/1990 | Bundy et al. | 606/180 |
| 5,135,531 | 8/1992 | Shiber | 606/180 |

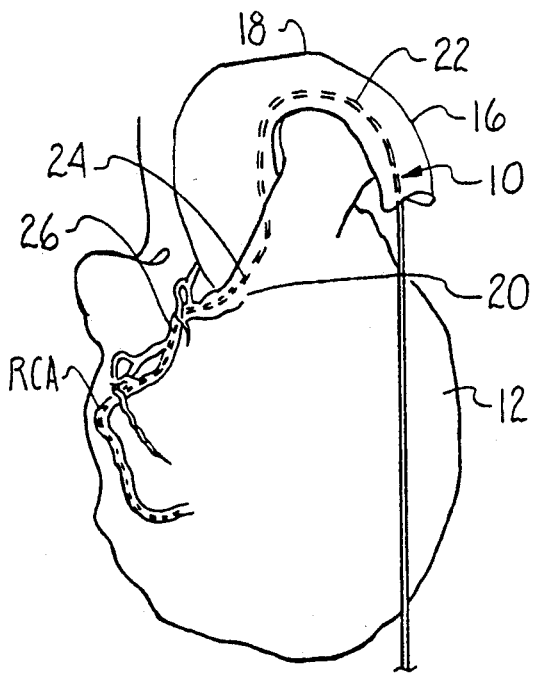
Fig.1
RIGHT CORONARY ARTERY
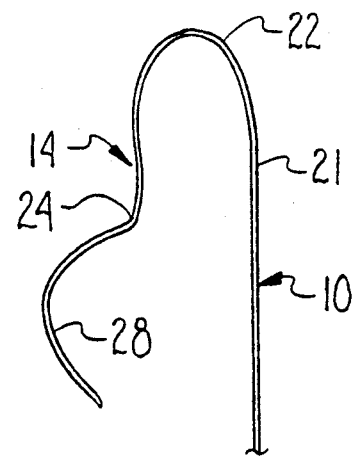
Fig.1A
Fig.1B
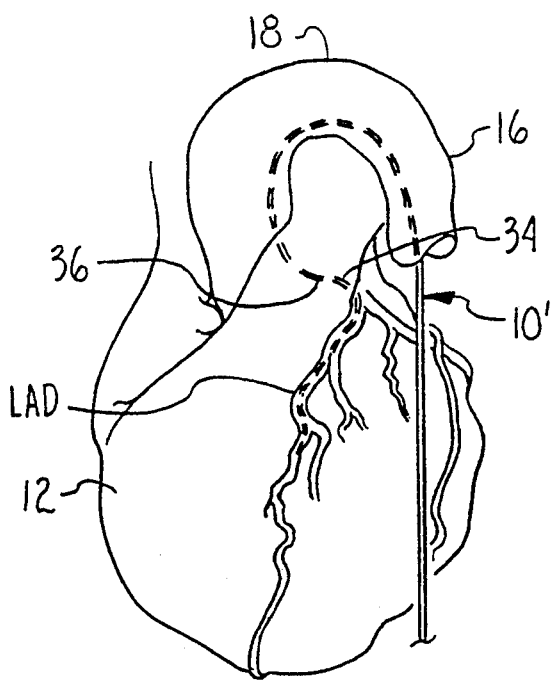
Fig.2
LEFT ANTERIOR DESCENDING
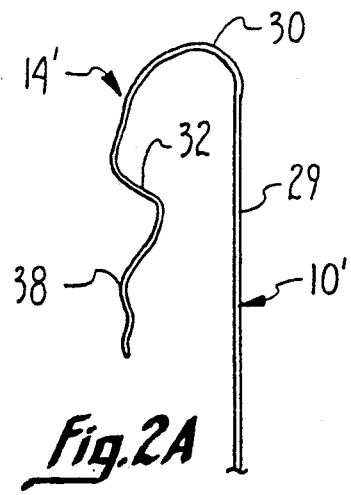
Fig.2A
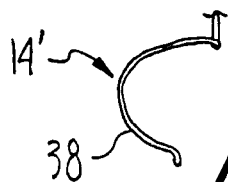
Fig.2B

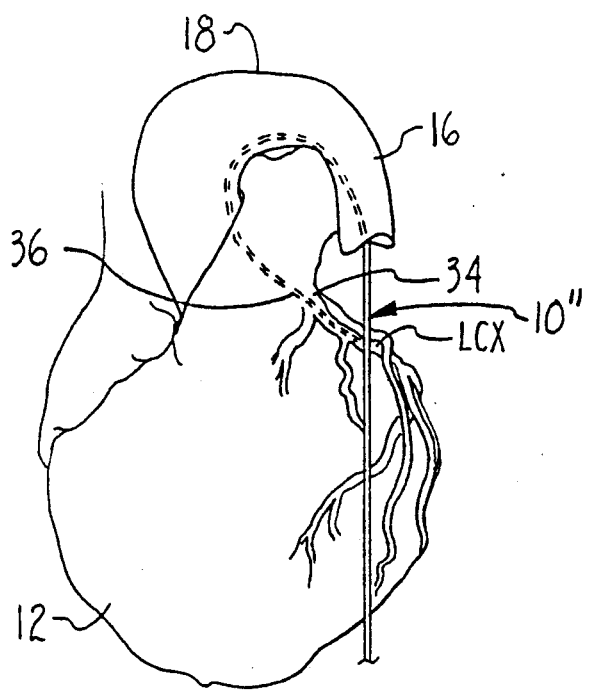
Fig. 3
LEFT CIRCUMFLEX ARTERY
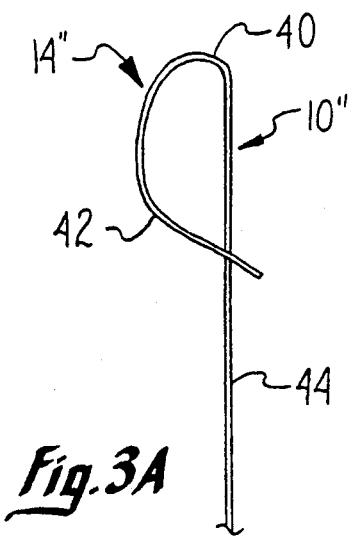
Fig. 3A
Fig. 3B
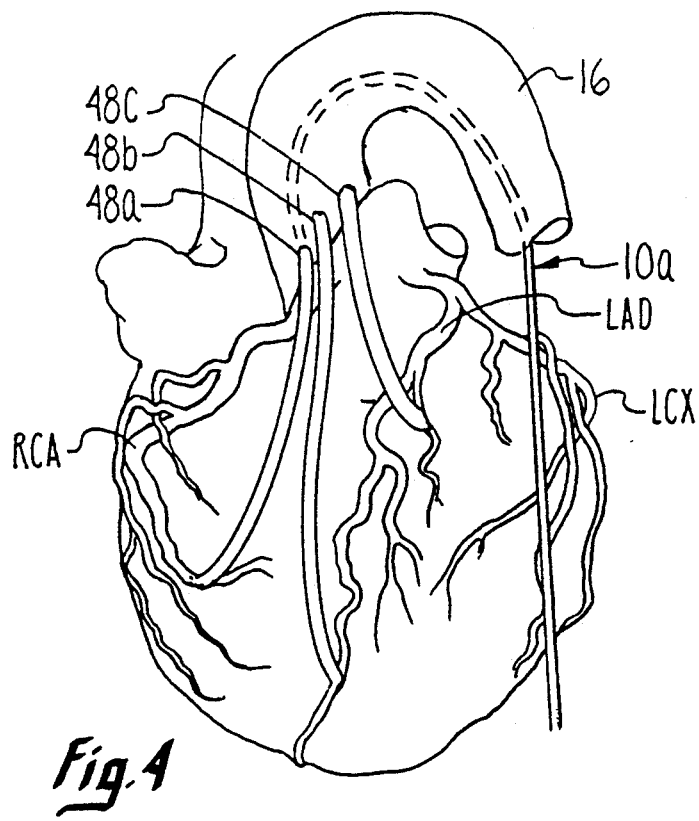
Fig. 4
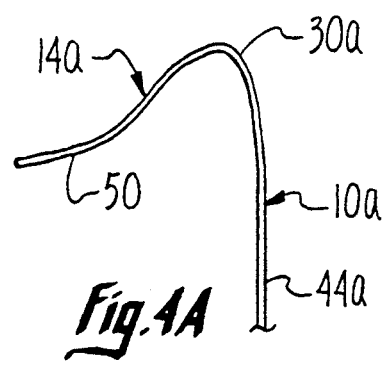
Fig. 4A
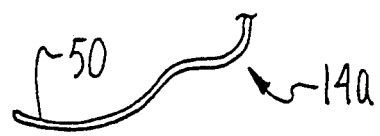
Fig. 4B

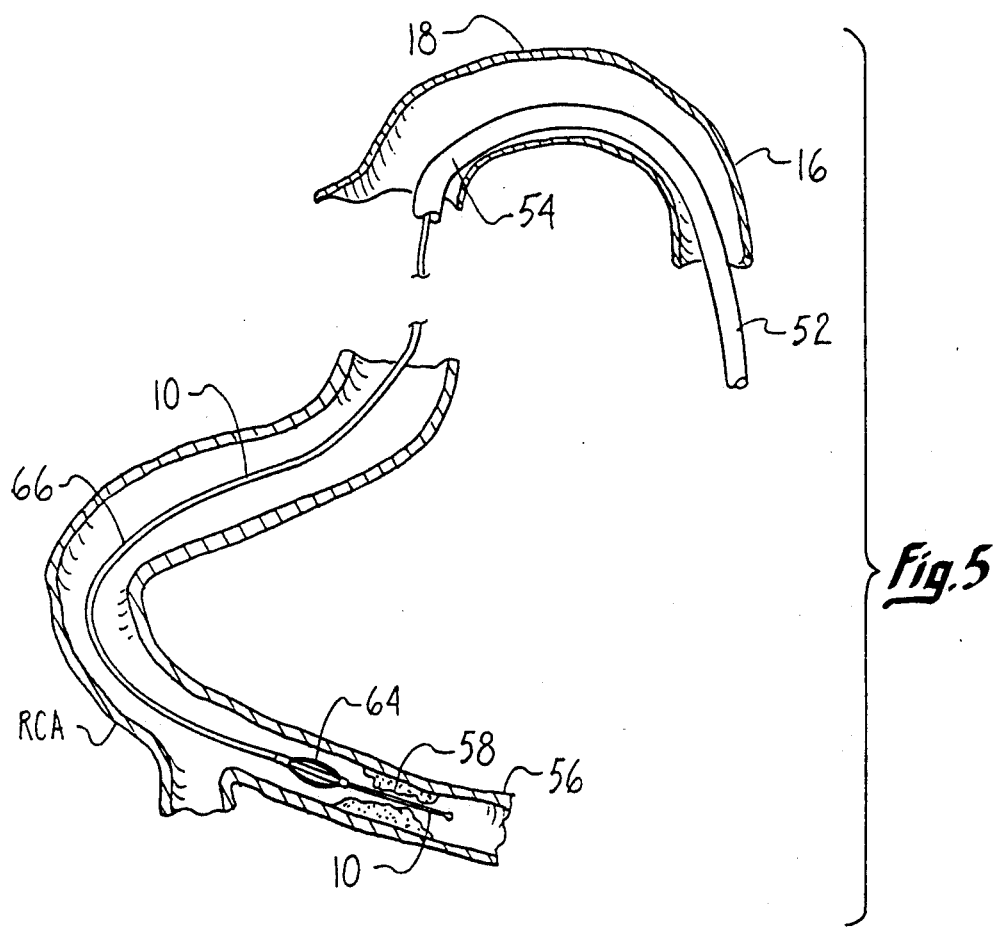
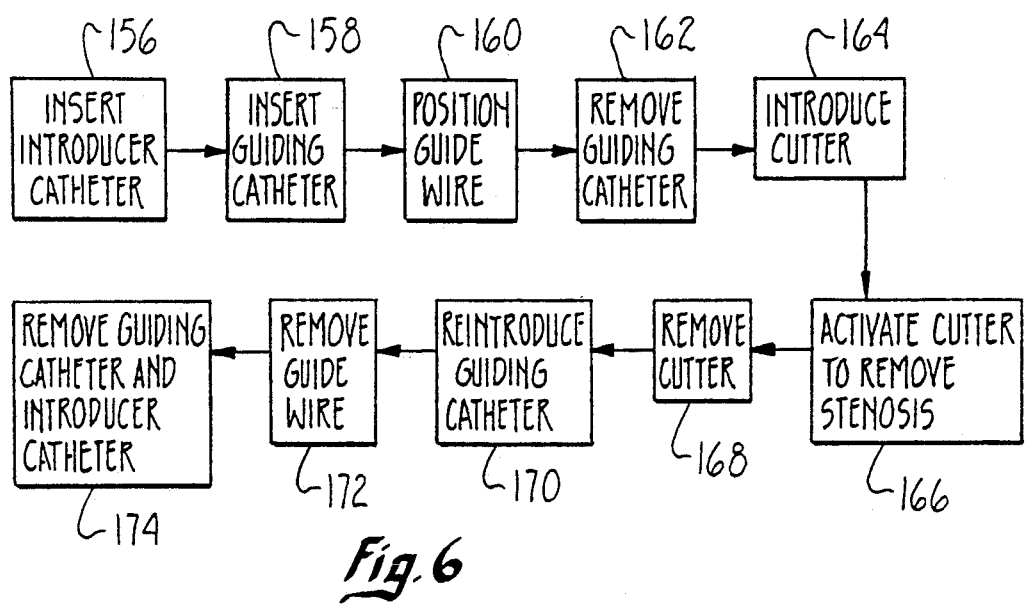

ANATOMICAL GUIDE WIRE

FIELD OF THE INVENTION

This is a divisional application of co-pending application Ser. No. 07,853,916 filed on Mar. 19, 1992.

The present invention relates generally to medical guide wires. More particularly, the present invention relates to guide wires for guiding an atherectomy cutter through a patient's blood vessel to position the cutter next to a stenosis to be removed. The present invention is particularly, though not exclusively, useful for guiding an atherectomy cutter into a coronary artery to relieve a stenosis in the artery.

BACKGROUND OF THE INVENTION

Arterial blockages caused by the build up of plaque in the arteries, as is well known, can have grave consequences. Of particular concern to the present invention is the build up of plaque in the coronary arteries, which can reduce and eventually block blood flow through the affected vessel. When blood flow through a coronary artery is reduced, the heart muscle is deprived of oxygen, and the patient is prone to suffer angina. In severe cases of coronary artery blockage, the patient can suffer a heart attack and death.

To alleviate stenoses of the coronary arteries, modern surgical techniques have been developed that include procedures wherein a portion of a blood vessel is grafted onto the affected coronary artery. This shunts blood around the stenosis and thereby restores blood flow to the part of the heart muscle that was deprived of blood. These so-called bypass surgery techniques have become relatively safe and effective in restoring blood flow to the heart muscle through the coronary arteries. Unfortunately, bypass surgery is invasive, and can consequently require significant post-operative recovery time. Consequently, alternative techniques have been developed wherein a medical device is inserted into the blocked artery over a guide wire and advanced along the guide wire until the device is at the stenosis. Once in place in the artery, the medical device is activated to relieve the stenosis.

An example of one such medical procedure is a balloon angioplasty procedure wherein a balloon is positioned adjacent the stenosis and fluid is infused through the catheter to inflate the balloon This inflation causes the balloon to compact the stenosis to alleviate the stenosis. After the stenosis has been compacted, fluid is withdrawn from the balloon to collapse the balloon, and the balloon is withdrawn from the artery. An example of one such angioplasty apparatus is the device disclosed in U.S. Pat. No. 4,799,479 to Spears.

In addition to balloon angioplasty devices, atherectomy cutting devices have been developed which can be advanced into a blocked artery over a prepositioned guide wire to mechanically cut through a stenosis and thereby remove the stenosis. An example of such an atherectomy device is disclosed in U.S. Pat. No. 4,887,613 to Farr et al., which teaches a rotatable catheter and a hollow cutter attached to the distal end of the catheter.

Independent of the particular type of medical apparatus to be used to alleviate the stenosis, it is necessary to properly position the apparatus. To do this, a guide wire is typically used and for obvious reasons, it is desirable that the guide wire maintain its position within the artery during the particular stenosis-removing procedure. In other words, once positioned within the artery, the guide wire should not loose its position within the artery.

It so happens that in certain body vessels, such as the coronary arteries, undesirable guide wire movement relative to the vessel can result in the wire becoming completely dislocated from the vessel. The problem with coronary arteries in prepositioning a guide wire is aggravated by the fact these arteries near the heart have relatively tortuous paths. Consequently, it is extremely difficult to position these guide wires and once positioned they are difficult to retrieve.

To reduce delays in repositioning a guide wire which has become inadvertently dislocated from a coronary artery, surgical techniques have been developed wherein the guiding catheter, through which the wire has been introduced into the body, is left in the aorta during the entire medical procedure. A pathway is thereby maintained through the guiding catheter for repositioning a potentially dislocated guide wire.

Unfortunately, in the case of atherectomy cutters, the size of the cutter and, hence, the width of the swath which the cutter can make through the stenosis are limited by the requirement that the cutter be small enough to pass through the guiding catheter. As indicated above, there are good reasons why it is sometimes preferable if the guiding catheter can be removed.

The present invention recognizes the need for using a guiding catheter to position a guide wire in a vessel having a complex tortuous path. The present invention, however, also recognizes the guide wire can be so positioned without requiring that the guiding catheter remain in the vessel with the guide wire during the entire stenosis-removing procedure. In addition the present invention recognizes the need for a guide wire that can be easily removed from the blood vessel without causing damage to the vessel.

Accordingly, it is an object of the present invention to provide a guide wire which is positionable within a vessel of a patient and which can be used in conjunction with a variety of medical apparatus for removing arterial stenoses. Another object of the present invention is to provide a guide wire which is positionable within a vessel, e.g., a coronary artery of a patient, to substantially maintain its position within the vessel. Still a further object of the present invention is to provide a guide wire that is easy to use and comparatively cost-effective to manufacture.

SUMMARY

A guide wire device in accordance with the present invention is positionable in a patient's vessel and can be slidably engaged with a medical apparatus, e.g. an atherectomy cutter, for advancing the apparatus over the wire into contact with a stenosis in a segment of the vessel. As intended for the present invention, the device includes an elongated flexible stainless steel wire which has a distal portion with a preformed anatomical shape when the distal portion of the wire is in an unstressed state. With this anatomical shape, the distal portion of the wire conforms to the shape of the segment of the vessel which has the stenosis.

As an example, the distal portion of the guide wire may correspond in shape to the arterial pathway from the apex of the aorta into an ostium of a major artery of the heart and then into the artery. This may include the right coronary artery (RCA), the left circumflex (LCX)

branch of the main left coronary artery, or the left anterior descending (LAD) branch of the main left coronary artery. Alternately, the distal portion of the guide wire may be shaped to enter the aorta and follow the pathway of a bypass graft formed in a major artery of the heart.

In one aspect of the operation of the present invention, a guiding catheter is percutaneously positioned through an introducer catheter and advanced into the aorta of the patient. A guide wire having an anatomical shape for conforming to the particular coronary artery or a bypass graft of an artery is then inserted through the guiding catheter. More specifically, the guide wire is inserted through the guiding catheter to position the preformed distal portion of the wire in the portion of the coronary artery that has been blocked by a stenosis. The guiding catheter is then withdrawn from the patient, and an atherectomy cutter is advanced over the wire, into the affected coronary artery, and against the stenosis. The cutter is then activated to cut through and remove the stenosis. After the cutter has cut through the stenosis, the cutter is withdrawn over the guide wire and removed from the patient.

Importantly, during insertion, activation, and removal of the cutter from the artery, the distal portion of the wire conforms to the anatomical shape of the aorta and coronary artery to hold the guide wire in its prepositioned place. After the cutter has been removed from the patient, the guiding catheter is again positioned in the aorta of the patient to permit retrieval of the wire from the patient through the guiding catheter. The guide wire is then removed from the patient through the guiding catheter. Subsequently, the guiding catheter is removed from the patient.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a left anterior oblique view of the heart showing the placement of the guide wire of the invention in the right coronary artery (RCA);

FIG. 1A is a side elevation view of the distal portion of the guide wire of the invention shaped for placement in the right coronary artery (RCA);

FIG. 1B is a plan view of FIG. 1A;

FIG. 2 is a left anterior oblique view of the heart showing the placement of the guide wire of the invention in the left anterior descending (LAD) branch of the main left coronary artery;

FIG. 2A is a side elevation view of the distal portion of the guide wire of the invention shaped for placement in the left anterior descending (LAD) branch;

FIG. 2B is a plan view of FIG. 2A;

FIG. 3 is a left anterior oblique view of the heart showing the placement of the guide wire of the invention in the left circumflex (LCX) branch of the main left coronary artery;

FIG. 3A is a side elevation view of the distal portion of the guide wire of the invention shaped for placement in the left circumflex (LCX) branch of the main left coronary artery;

FIG. 3B is a plan view of FIG. 3A;

FIG. 4 is a left anterior oblique view of the heart showing three common locations for bypass grafts;

FIG. 4A is a side elevation view of a portion of the distal portion of the guide wire of the invention shaped for placement in a bypass graft;

FIG. 4B is a plan view of FIG. 4A;

FIG. 5 is an enlarged side elevation view of the guide wire of the present invention positioned in the right coronary artery (RCA) as shown in FIG. 1 with portions shown in cross-section and portions broken away for clarity; and FIG. 6 is a block diagram showing the steps involved with the method of the invention.

DESCRIPTION OF THE PREFERRED EMBODIMENT

Referring initially to FIGS. 1 and 1A, an anatomically-shaped guide wire 10 formed in accordance with the present invention is shown in place in the right coronary artery.(RCA) of a patient's heart 12. The guide wire 10 is an elongated flexible structure which is made of a suitably strong material such as stainless steel, tungsten, or titanium that can be formed and maintained in a desired shape. The guide wire 10 is preferably a solid wire having a diameter that is between approximately twenty five thousandths and thirty thousandths of an inch (0.025"–0.030").

For treating a stenosis in the right coronary artery (RCA), the guide wire 10 must be placed into the aorta 16, threaded over the apex 18 of the aorta, and then into the ostium 20 of the right coronary artery (RCA) formed at the aorta 16. The guide wire 10 is preformed such that a distal portion 14 of the guide wire 10 is shaped to maintain the placement of the guide wire 10 in the aorta 16 and right coronary artery (RCA) of the heart 12.

As shown in FIG. 1A and 1B, the distal portion 14 of the guide wire 10 conforms to the general anatomical shape or arterial path from the aorta 18 and into the right coronary artery (RCA). This shape includes a straight portion 21 that corresponds to the arterial path through the rib cage and into the aorta 16. A 180 degree bend portion 22 of the guide wire 10 corresponds to the 180 degree bend at the apex 18 of the aorta 16. An outwardly directed and radiused portion 24 of the guide wire 10 corresponds to the placement and shape of a main branch 26 (FIG. 1) of the right coronary artery (RCA) as it extends from its ostium 20 at the aorta 18 and its path into the heart 12. A generally hemispherical shaped portion 28 of the guide wire 10 corresponds to the location of the main branch 26 of the right coronary artery (RCA) as the artery extends in a generally circumferential direction along the periphery of the heart 12 towards the left ventricle of the heart 12 and then branches into marginal branches. The distal portion 14 of the guide wire 10 is preferably formed in a three dimensional shape that conforms to this three dimensional arterial path into the right coronary artery (RCA) and of the (RCA) in the heart.

Referring now to FIGS. 2, 2A and 2B a guide wire 10' is shown that conforms to the general anatomical shape and arterial pathway into the left anterior descending (LAD) artery of the heart. As such, the guide wire 10' includes a straight portion 29 which corresponds to the arterial pathway through the rib cage and into the aorta 16. The guide wire 10' also includes a distal end 14', having a 180 degree bend portion 30, that corresponds to the 180 degree bend at the apex 18 of the aorta 16. A inwardly directed and radiused portion 32 of the guide wire 10' corresponds to the placement and path of the main left coronary artery 34 at its ostium 36 with the aorta 16 and as it branches into the left interior descending (LAD) artery. A large generally radiused portion 38 of the guide wire 10' corresponds to the path of the left anterior descending artery (LAD) as it follows the outer circumferential surface of the heart 12 in a descending direction. As before, the distal portion 14' of the guide wire 10' is preferably formed in a three dimensional shape that conforms to a three dimensional path into the left anterior descending artery (LAD) and of the (LAD) in the heart.

Referring now to FIGS. 3, 3A and 3B a guide wire 10" is shown that conforms to the general anatomical shape and arterial pathway into the left circumflex artery (LCX) of the heart 12. As such, the guide wire 10", includes a distal end 14", having a straight portion 44, and a 180 degree bend portion 40, that corresponds to the 180 degree bend at the apex 18 of the aorta 16. An inwardly angled portion 42 corresponds to the placement and path of the main left coronary artery 34 at its ostium 36 with the aorta 16 and corresponds to its path as it branches into the left circumflex artery (LCX) of the heart. The inwardly angled portion 42 of the guide wire 10" then bends inward towards the straight portion 44 of the guide wire 10" in correspondence with the direction of the left circumflex artery (LCX) as it descends and curves around the outer periphery of the heart 12. As before, the distal portion 14" of the guide wire 10" is preferably formed in a three dimensional shape that conforms to a three dimensional path into the left circumflex (LCX) and of the path of artery into the heart.

Referring now to FIGS. 4, 4A and 4B a guide wire 10a especially adapted for placement in a bypass graft of the heart is shown. Three common locations for a bypass graft are shown in FIG. 4 and are designated as 48a, 48b, or 48c. In general a bypass graft, 48a, 48b, or 48c, shunts the flow of blood from the aorta 16 around a stenosis in a major artery of the heart. As shown in FIG. 4, this may include a bypass from the aorta 16 to the RCA, or a branch of the LAD. Other bypass locations however, are also possible As shown in FIGS. 4A and 4B, the distal portion 14a of the guide wire 10a has a 180° bend portion 30a that corresponds to the 180° bend at the apex 18 of the aorta 16. In addition the guide wire 10a is formed with a curved portion 50 that is shaped to correspond to a particular bypass graft (i.e. 48a, 48b, or 48c). As such the curved portion 50 of the guide wire 10a, corresponds to the path of the bypass graft as its ostium at the aorta and follows the path of the bypass graft (i.e. 48a, 48b, or 48c) into the heart 12. As before a straight portion 44a of the guide wire 10a corresponds to a straight arterial path into the apex 18 of the aorta 16.

One atherectomy system which can be used with guide wire 10 is shown in FIG. 5. Specifically, a hollow introducer catheter (not shown) can be percutaneously inserted into the patient to establish an entry site. A hollow guiding catheter 52 can then be introduced through the introducer catheter into aorta 16 and a distal end 54 of guiding catheter 52 positioned within the aorta 16 adjacent the right coronary artery (RCA). Guide wire 10 can be advanced through guiding catheter 52 into right coronary artery RCA and distal portion of guide wire 10 positioned in a segment 56 of right coronary artery RCA which has a stenosis 58. For purposes of disclosure, segment 56 of RCA includes that segment of RCA which extends from the aorta 16 and the juncture of a transverse branch of RCA and the descending branch of RCA into the branch. It is to be understood, however, that wire 10 can be used in conjunction with atherectomy or angioplasty applications in body vessels other than RCA (i.e. LAD, LCX, bypass graft). In such applications, distal portion 14 of wire 10 will be appropriately shaped to conform to the shape of the particular vessel.

Once distal portion 14 of wire 10 is positioned within segment 56 of RCA, distal portion 14 is no longer constrained by guiding catheter 52. Consequently, distal portion 14 assumes its unstressed shape within segment 56, i.e., distal portion 14 conforms to the shape of segment 56. Guiding catheter 52 is then retracted from the patient, and an atherectomy cutter 64 is slidingly engaged with wire 10 and inserted into aorta 16 over wire 10 as shown in FIG. 5.

More specifically, as can been seen in FIG. 5, cutter 64 is inserted into the patient and advanced over wire 10 into RCA against stenosis 58. As shown, cutter 64 is attached to the distal end of an atherectomy catheter 66. Once positioned against stenosis 58, cutter 64 can be activiated to excise stenosis 58 and remove stenosis 58 from the RCA through atherectomy catheter 66 by means well known in the art. After stenosis 58 has been excised, cutter 64 is retracted from the patient and guiding catheter 52 reintroduced into aorta 16 over wire 10. With guiding catheter 52 so positioned, wire 10 can be relatively easily retracted from the patient.

OPERATION

In the operation of guide wire 10, reference is made to FIGS. 5 and 6. As indicated at block 156 in FIG. 4, an introducer catheter is percutaneously inserted into the patient. Then, as indicated at block 158, a guiding catheter 52 is inserted through the introducer catheter and into aorta 16. The distal end 54 of guiding catheter 52 is positioned adjacent RCA. Next, guide wire 10 is advanced through guiding catheter 52 and the distal portion 14 of the guide of wire 10 is positioned across the stenosed segment 58 or RCA, as indicated at block 160. When guide wire 10 is positioned as disclosed, the distal portion 14 of the guide wire conforms to the shape of RCA.

Once guide wire 10 has been positioned as described, guiding catheter 52 is removed from the patient, as indicated at block 162. Because the distal portion 14 of wire 10 conforms to the shape of RCA, wire 10 maintains its position within RCA substantially as shown in FIG. 5. Cutter 64 is slidably engaged with wire 10 and is passed through introducer catheter.

Cutter 64 is advanced over wire 10 to a position against stenosis 58, and is activated to remove stenosis 58 from RCA, as indicated at block 166. More specifically, atherectomy catheter 66 and cutter 64 are rotated while cutter 64 is advanced over wire 10 into stenosis 58 to excise stenosis 58. Cut pieces of stenosis 58 are drawn into cutter 64. These cut pieces of stenosis 58 can be removed from the interior of cutter 64 through atherectomy catheter 66 by establishing a vacuum within atherectomy catheter 66.

After removal of stenosis 58 from RCA, cutter 64 and atherectomy catheter 66 are removed from the patient through guiding catheter 52, as indicated at block 168. As indicated at block 170 of FIG. 6, guiding catheter 52 is reintroduced into aorta 16 over wire 10 to the position substantially as shown in FIG. 5, to establish a pathway for retrieving guide wire 10. When guiding catheter 52 is in the position shown in FIG. 5, guide wire 10 can be relatively easily withdrawn through guiding catheter 52 from RCA, as indicated at block 172. This is necessary in order to eliminate any binding or snagging of wire 10 in RCA that might otherwise occur. After guide wire 10 has been removed from the patient, guiding catheter 52 and the introducer catheter are removed from the patient, as indicated at block 174. The preformed shape of the guide wire also aids in its effective removal without damage to the associated artery.

While the particular anatomical guide wire as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An apparatus for introducing a medical cutter into a coronary artery, to incise a stenosis in the artery, which comprises:
   a guide wire having an anatomically shaped distal non-straight portion, said distal portion being shaped to conform to a segment of an arterial pathway when in an unstressed state;
   a guiding catheter engageable with said guide wire, said distal portion of said guide wire being extendable from said guiding catheter to position and maintain said distal portion of said guide wire in said segment of said pathway of the coronary artery in said unstressed state; and
   an atherectomy cutter slidingly engageable with said guide wire for advancement along said guide wire and into contact with said stenosis.

2. An apparatus as recited in claim 1 wherein said guide wire is flexible throughout its length.

3. An apparatus as recited in claim 1 wherein said distal portion is elongated and has a preformed shape to conform to an arterial path from the aorta through a right coronary artery (RCA) including a 180° bend corresponding to an apex of the aorta, a curved portion corresponding to a path through the ostium of the (RCA) and a generally hemispherical portion corresponding to a path of the (RCA) through the heart.

4. An apparatus as recited in claim 1 wherein said distal portion is elongated and has a preformed shape to conform to an arterial path from the aorta through a left circumflex (LCX) branch of a left coronary artery including a 180° bend corresponding to an apex of the aorta, a curved portion corresponding to a path through the ostium of the (LCX) and a radiused portion corresponding to the path of the (LCX) through the heart.

5. An apparatus as recited in claim 1 wherein said distal portion is elongated and has a preformed shape to conform to an arterial path from the aorta through a left anterior descending (LAD) branch of a left coronary artery including a 180° bend corresponding to the apex of the aorta, an inwardly angled portion corresponding to a path through the ostium of the (LAD) and path of the (LAD) through the heart.

6. An apparatus as recited in claim 1 and wherein said distal portion is elongated and has a preformed shape for following the arterial path of a bypass graft including a generally hemispherical shaped bent portion.

7. An apparatus as recited in claim 1 further comprising an end cap formed on said distal portion of said guide wire for confining said medical cutter to movement along said guide wire.

8. A method for removing a stenosis from a coronary artery of a patient which comprises the steps of:
   positioning a guiding catheter into the aorta of the patient;
   inserting a guide wire having an anatomically shaped distal non-straight portion through said guiding catheter, said distal portion being shaped to conform to a segment of an arterial pathway when said distal portion is in an unstressed state, said distal portion of said guide wire being extendable from said guiding catheter to position said distal portion of said guide wire in said coronary artery and against said stenosis;
   withdrawing said guiding catheter from the patient;
   advancing an atherectomy cutter over said prepositioned guide wire and into contact with said stenosis in said coronary artery for removal of said stenosis by operation of the cutter;
   withdrawing said atherectomy cutter from the patient;
   repositioning said guiding catheter in the aorta of the patient;
   retrieving said guide wire from the patient through said guiding catheter; and
   removing said guiding catheter from the patient.

9. A method as recited in claim 8 wherein said guide wire includes a straight portion and a 90° portion that corresponds in shape to an apex of the aorta.

10. A method as recited in claim 8 wherein said guide wire is shaped to correspond to an arterial path from the aorta through a right coronary artery (RCA).

11. A method as recited in claim 8 wherein said guide wire is shaped to correspond to an arterial path from the aorta through a left anterior descending (LAD) artery.

12. A method as recited in claim 8 wherein said guide wire is shaped to correspond to an arterial path from the aorta through a left circumflex (LCX) artery.

13. A method as recited in claim 8 wherein said guide wire is shaped to correspond to an arterial path from the aorta and through a bypass graft formed in an artery of the heart.

14. A method for removing a guide wire from a coronary artery to prevent binding or snagging of the guide wire during withdrawal of the guide wire through the artery, the guide wire having a preformed non-straight distal portion which, in an unstressed state, is shaped to specifically conform to a segment of the arterial pathway, the method comprising the steps of:
   advancing a guiding catheter along said guide wire to establish a path in the artery, said path providing means for isolating the artery from stress forces developed in said distal portion during withdrawal of said guide wire from the artery through said guiding catheter;
   withdrawing said guide wire through said guiding catheter; and
   removing said guiding catheter from the artery.

15. A method as recited in claim 14 wherein said advancing step is accomplished by advancing said guiding catheter to where only said distal portion of said guide wire extends from said guiding catheter.